United States Patent [19]

Christe et al.

[11] Patent Number: 4,476,337

[45] Date of Patent: Oct. 9, 1984

[54] METHOD FOR INTRODUCING FLUORINE INTO AN AROMATIC RING

[75] Inventors: Karl O. Christe, Calabasas; Carl J. Schack, Chatsworth, both of Calif.

[73] Assignee: The United States of America as represented by the Secretary of the Air Force, Washington, D.C.

[21] Appl. No.: 534,030

[22] Filed: Sep. 20, 1983

Related U.S. Application Data

[62] Division of Ser. No. 343,033, Jan. 27, 1982, Pat. No. 4,423,260.

[51] Int. Cl.³ .............................................. C07C 17/04
[52] U.S. Cl. .................................... 570/148; 570/147
[58] Field of Search ................................ 570/147, 148

[56] References Cited

U.S. PATENT DOCUMENTS 3,235,608  2/1966  Gibbs ................................. 570/148

Primary Examiner—Charles F. Warren
Assistant Examiner—Joseph A. Boska
Attorney, Agent, or Firm—Donald J. Singer; William J. O'Brien

[57] ABSTRACT

A process for introducing a fluorine atom into an aromatic hydrocarbon by effecting a substitution reaction between an aromatic hydrocarbon and an $NF_4^+$ cation containing salt.

4 Claims, No Drawings

METHOD FOR INTRODUCING FLUORINE INTO AN AROMATIC RING

STATEMENT OF GOVERNMENT INTEREST

The invention described herein may be manufactured and used by or for the Government for governmental purposes without the payment of any royalty thereon. This is a division of application Ser. No. 343,033, filed Jan. 27, 1982, now U.S. Pat. No. 4,423,260.

FIELD OF THE INVENTION

This invention relates to fluorocarbons and to a novel method for their synthesis. In a more particular aspect, this invention concerns itself with a novel method for introducing a fluorine atom into an aromatic ring.

Aromatic fluorocarbons are a well known class of chemical compounds that find wide utility for a variety of industrial applications and in the fabrication of various commercial products. They are useful as solvents, electrical fluids, heat transfer fluids and as components in the manufacture of resins, waxes, greases and oils. However, presently known methods for synthesizing such compounds by introducing a fluorine atom into an aromatic ring structure are severely limited.

The classic Balz-Schiemann reaction, for example, and methods such as the decarboxylation of flurofor-mates are useful for the introduction of a single fluorine atom, but are generally less useful for multiple fluorine substitution. The use of elexental fluorine or electrochemical fluorination methods result mainly in addition and not in substitution. Halogen fluorides, such as $ClF_3$, $BrF_3$, or $IF_5$, produce, in addition to fluorine substituted compounds, large amounts of the corresponding halogen substituted compounds and also some addition products. The yield of substitution products obtainable with halogen fluorides can be improved by the use of strong Lewis acids. However, the extreme reactivity of the resulting compounds, such as $ClF_2^+ BF_4^-$ or $ClF_2^+ SbF_6^-$, makes control of their reactions with organic compounds extremely difficult and unsafe. The utilization of transition metal fluorides, such as $CoF_3$ or $CeF_4$ results in addition and saturation, requiring subsequent rearomatisation. Therefore, this method is limited to highly or perhalogenated aromatics. Pyrolysis of aliphatic fluorocarbons, such as $CFBr_3$, can also produce fluoroaromatics. However, this method is limited again to the synthesis of perfluorinated aromatics. Halogen exchange reactions, such as Cl versus F, using HF, alkali metal or metal fluorides are useful, but are restricted to systems strongly activated towards nucleophilic attack by fluoride ion. Hypofluorites, such as $CF_3OF$, are useful for electrophilic and photolytic fluorinations. The electrophilic fluorinations are limited again to activated aromatics, whereas the free radical photolytic fluorinations often lack selectivity resulting in $-OCF_3$ substituted by-products and side chain fluorination. The xenon fluorides and especially $XeF_2$ are promising reagents for electrophilic aromatic substitution, but the full extent of their usefulness is still unknown. The limited availability of xenon, its high price, and the treacherous explosiveness of their hydrolysis product, $XeO_3$, are drawbacks curtailing its extensive use.

The above listing of some of the known methods of preparing aromatic fluorine compounds, although not extensive, clearly illustrates the problems prevalent in this area of technology and points out the need for a reliable, readily available and economically feasible reagent for accomplishing the electrophilic fluorine substitution of aromatic ring compounds. Therefore, a research effort was undertaken in an attempt to satisfy the need for a generally usable reagent.

In theory, the ideal reagent for electrophilic substitution would be a salt containing the $F^+$ cation. Unfortunately, such salts do not exist. As an alternative, salts containing complex fluoro cations of the type $XF_{(n+1)}^+$ could be used. However, to be a strong electrophile, such a cation should possess high electronegativity. Since highly electronegative fluorine compounds generally are very strong oxidizers, most of these cations react too violently with organic compounds to be of practical interest. As a consequence, the research effort referred to above proved to be unsuccessful. Additional research, however, proved to be fruitful and culminated in the discovery that the $NF_4^+$ cation constitutes an exception to the general rule that such cations react too violently with organic compounds. As a result of the present invention, therefore, it was found that aromatic ring compounds, such as benzene, toluene, and nitrobenzene, interact rapidly with $NF_4BF_4$ in anhydrous HF to give, almost exclusively, fluorine substituted aromatic derivatives.

SUMMARY OF THE INVENTION

The present invention concerns itself with a method for introducing fluorine into an aromatic ring structure by using $NF_4BF_4$ as a reaction reagent. The introduction is accomplished by an electrophilic substitution reaction in which up to five hydrogen atoms in the aromatic ring can be substituted by fluorine atoms. The reaction can be carried out by either adding the aromatic compound, such as benzene in vapor form, to a cooled solution of $NF_4BF_4$ in HF or, alternatively, by adding slowly a solution of $NF_4BF_4$ to a solution of benzene in HF.

Accordingly, the primary object of this invention is to provide a novel xethod for introducing a fluorine atom into an aromatic ring structure.

Another object of this invention is to provide a method for substituting fluorine atoms for the hydrogen atoms in an aromatic ring structure.

Still another object of this invention is to provide for the synthesis of fluorine containing aromatic ring compounds by effecting a reaction between a non-fluorine containing aromatic compound and salts containing an $NF_4^+$ cation.

A further object of this invention is to provide a method for introducing a fluorine atom into an aromatic ring by using $NF_4BF_4$ as a reaction reagent in the electrophilic substitution of a fluorine atom for a hydrogen atom in an aromatic ring structure.

The above and still further objects and advantages of the present invention will become more readily apparent upon consideration of the following detailed description thereof.

DETAILED DESCRIPTION OF THE PREFERRED EMBODIMENT

Pursuant to above-defined objects, the present invention concerns itself with a novel method for introducing fluorine atoms into an aromatic ring compound through the electrophilic substitution of a hydrogen atom by a fluorine atom. The known methods for introducing fluorine into an aromatic ring are quite limited and are often not generally applicable. A widely applicable reagent for carrying out electrophilic substitution reactions on aromatic ring systems, therefore, would be highly desirable. As a result, a concentrated research effort was undertaken based on the hypothesis that the use of $NF_4^+$ ion containing salts in this regard would be promising. A continued investigation of aromatic hydrocarbon reactions with $NF_4^+$ ion containing species confirmed the hypothesis. It was found that a reaction between an aromatic hydrocarbon ring compound, such as benzene, toluene or nitrobenzene with an $NF_4^+$ salt accomplished the substitution of up to five hydrogen atoms in the aromatic ring by fluorine atoms.

Hydrogen fluoride was used as a solvent because of the high solubility of $NF_4^+$ salts in it and also because the diluent and heat dissipation properties of a solvated system were found to be beneficial in the anticipated vigorous fluorination. As stated hereinbefore, the reaction was carried out by either adding benzene vapor to a cooled solution of $NF_4BF_4$ in HF or by adding slowly a solution of $NF_4BF_4$ to a solution of benzene in HF. On contact gas evolution was noted. When rapid addition occurred some apparent charring occurred. The stepwise substitution of H by F was observed according to the following general equation:

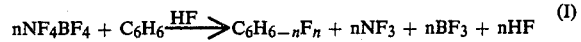

$$nNF_4BF_4 + C_6H_6 \xrightarrow{HF} C_6H_{6-n}F_n + nNF_3 + nBF_3 + nHF \quad (I)$$

(where n = 1–5)

The evolved gas was removed under vacuum and trapped at $-196°$ C. It was found to be $NF_3$ and the amount corresponded to that expected on the basis of one mole of $NF_3$ per mole of $NF_4BF_4$. Hexafluorobenzene was not observed although all other substitution products from mono-to-penta-fluorobenzene were obtained. Almost no saturated or partially saturated fluorocarbons were produced which makes this process of special interest in generating aromatic fluorocarbons directly from their hydrocarbon analogues.

The benzene, toluene, and nitrobenzene reactants interacted rapidly with $NF_4BF_4$ in anhydrous HF to give, almost exclusively, fluorine substituted aromatic derivatives. With benzene, up to five hydrogens were replaced, while a maximum of four hydrogens were displaced in $C_6H_5CH_3$ and $C_6H_5NO_2$. The direction of the substitution in $C_6H_5CH_3$ and $C_6H_5NO_2$ and the lack of side chain fluorination in $C_6H_5CH_3$ support an electrophilic substitution mechanism when using $NF_4BF_4$ as a reactant. Although highly electronegative fluorine compounds generally are very strong oxidizers, most cations react too violently with organic compounds to be of practical interest. The $NF_4^+$ cation, however, was found to be an exception. It combines high electronegativity (oxidation state of +V) with high kinetic stability (it is isoelectronic with $CF_4$), and its reactions require significant activation energies. Furthermore, $NF_4^+$ salts, such as $NF_4BF_4$, offer the advantage of generating in an electrophilic aromatic substitution reaction only by-products, such as $NF_3$ and $BF_3$, which are unreactive toward the organic compounds. In view of these properties and its ready availability, $NF_4BF_4$ was found to be an ideal candidate for electrophilic aromatic substitution reactions. A vigorous ring hydrogen substitution occurred even at $-7.8°$ C. in HF solution.

In carrying out the reactions of this invention, the nonvolatile materials were manipulated in a well-passivated (with $ClF_3$) stainless steel vacuum line equipped with Teflon FEP U traps, 316 stainless steel bellows seal valves and a Heise Bourdon tube-type pressure gauge. Hydrogen fluoride work was carried out in an all Monel and Teflon vacuum system. Transfers outside the vacuum line were carried out in a drybox. Infrared spectra were obtained using 5 cm path stainless steel cells with AgCl windows and a PE Model 283 spectrophotometer. Mass spectra were measured with an EA1 Quad 300 quadrupole spectrometer and $^{19}F$ and $^1H$ nmr spectra were determined with a Varian EH390 spectrometer operating at 84.6 and 90 MHz, using $CFCl_3$ or TMS as internal standards, respectively. Positive chemical shifts are upfield from $CFC_3$ and downfield from TMS. Raman spectra were recorded on a Cary Model 83 using the 4880 Å exciting line. Gas chromatographic data were obtained using a Varian Aerograph GC with a thermal conductivity detector under isothermal conditions (135°) with a stainless steel column ($\frac{1}{8}'' \times 10'$) packed with Poropak PS. For the GC determination of the quantitative composition of mixtures, uncorrected peak areas were used since response factors were not available for all compounds. The solid $NF_4BF_4$ was prepared from $NF_3$—$F_2$—$BF_3$ at low temperature using UV activation, which gives analytically pure material.

The simplest aromatic hydrocarbon studied in the previously referred to research effort was benzene. With $NF_4^+$ substrate mole ratios of about three, up to five hydrogens were substituted by F as shown in the following generalized equation.

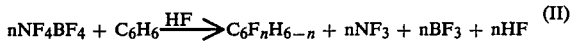

$$nNF_4BF_4 + C_6H_6 \xrightarrow{HF} C_6F_nH_{6-n} + nNF_3 + nBF_3 + nHF \quad (II)$$

where n = 1–5

However, at these higher $NF_4^+$ to substrate ratios, the reaction was more difficult to control and more "char" formation was noted. Hexafluorobenzene was not observed as a product. If significant amounts had been formed, it would have easily been detected by mass spectroscopy since its base peak is the parent ion. Only trace quantities of partially saturated species, $C_6F_6H_2$ and $C_6F_7H$ were observed, indicating that very little addition occurred.

In order to determine the nature of the reaction, two substituted benzenes, $C_6H_5CH_3$ and $C_6H_5NO_2$ were also studied. These were chosen for their well known ability to differentiate between an electrophilic and a free radical reaction path, based on the observed ortho-meta-para product distribution.

In the toluene reaction, the ratio of $NF_4^+$ to toluene was in the range 2-4:1. Thus, an excess of fluorine was available (assuming one $F/NF_4^+$ is available for substitution) and multisubstitution was expected. The result of a very rapid reaction is illustrated by the following equation:

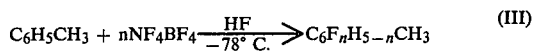

$$C_6H_5CH_3 + nNF_4BF_4 \xrightarrow[-78° C.]{HF} C_6F_nH_{5-n}CH_3 \quad (III)$$

where n = 1–4

The mass spectra of the products strongly indicate that no side chain fluorination had occurred, in agreement with other spectroscopic evidence. Typical isomer distributions for the ring substitution were: o-F(15), m-F(8), p-F(15), 2,4 di-F(30), and mixed di- and tri-F(25). Obviously, o- and p- products predominate for this electron rich ring, a result which is compatible with an electrophilic substitution process.

For the nitrobenzene reaction, a 3:10 mole ratio of $NF_4BF_4F$: substrate was used. Even under these conditions, this reaction was less vigorous than those of benzene or toluene, as exemplified by a slightly slower $NF_3$ evolution and the lack of "darkening" of the solution until the mixture was finally warmed to about 0°. Fluorine substitution occurred to give $C_6F_nH_{5-n}NO_2$ (where n=1-4) compounds. Minor amounts of $FNO_2$ $(HF)_n$ were formed and traces of $C_6F_nH_{6-n}$ species were observed, but overwhelmingly the $NO_2$ group was not displaced. The observed products were mainly monosubstituted with the following isomer distribution: o-F(16), m-F(62), and p-F(7).

The observation of predominantly ortho and para substitution and the lack of side chain fluorination in toluene, and the meta substitution in nitrobenzene establishes these $NF_4BF_4$ reactions as electrophilic substitutions.

For nitrobenzene, the yield of fluorinated products was not determined due to separation problems caused by the low volatility of the products and the large excess of nitrobenzene used. However, in view of the high relative amount of mono-F species, and the limited amount of charring, it is estimated that the yield of substituted products was high. For the much more reactive $C_6H_6$ and $C_6H_5CH_3$, yields varied widely. Volatile, fluorinated species were observed equivalent to 30–60% of the aromatic starting compounds.

The following examples are presented in order to point out the invention with greater detail. The examples, however, are illustrative only and are not to be construed as limiting the invention in any way.

EXAMPLE I $C_6H_5NO_2$. To a stirred solution of $C_6H_5NO_2$ (10 mmol) in 5 ml HF at -78° was added dropwise over 30 min. a solution of $NF_4BF_4$(2.88 mmol) in 5 ml HF. Reaction of the $NF_4BF_4$ was shown by an increase in pressure due to $NF_3$ evolution. When all the $NF_4BF_4$ had been added, the reaction was gradually warmed to 0° C. and left overnight. During the warming, the reaction solution changed from pale yellow to dark brown. Keeping the reaction ampoule at −45°, the $NF_3$, HF, and other volatile materials were pumped away through −78° and −196° C. traps. After the majority of the HF was removed, the reactor was maintained at 0° C. The material passing the −78° C. fraction consisted of a few droplets of a liquid with a low vapor pressure at ambient temperature. Mass spectroscopy of the vapor from the drops showed minor amounts of aromatic fluorocarbons which did not contain $NO_2$ substituents. These were of the empirical formula $C_6F_nH_{6-n}$(n=1-4). The principal ion peaks observed were m/e (assign.): 85($NO_2F$ HF), 49 (NOF), and 30(NO). Examination of the liquid non-volatiles at 0° C. which remained in the reactor, by NMR spectroscopy, showed that five fluorinated compounds were present and all were found to be substituted nitrobenzenes by comparison of the observed chemical shifts with reported values. By measurement of the area of the resonances the amount of each compound was calculated: o-$C_6FH_4NO_2$(14%), m-$C_6FH_4NO_2$(62%), p-$C_6FH_4NO_2$ (6%), 2,6-or 3,5-difluoronitrobenzene (14%), and 2,4-difluoronitrobenzene. The large excess of $C_6H_5NO_2$ C employed, and still present, masked the $^1H$ spectra of these products and thus the $^{19}F$ spectra were relied on for identification.

EXAMPLE II $C_6H_5CH_3$. Toluene and $NF_4BF_4$(1:4 molar ratio) were reacted by condensing the hydrocarbon onto the stirred HF solution of the salt at −78° C. Alternatively, toluene in HF at −78° C. was treated dropwise with a solution of $NF_4BF_4$ (1:2 molar ratio). In either case, instantaneous reaction occurred and the solution became black. After warming to 0° C. for a few hours, these reactions were worked up in the usual manner. Much tar like residue remained in the reactor in each case. Infrared spectroscopic examination of the volatile species, trapped at −78° C., showed strong bands near 1500 cm$^{-1}$ confirming the presence of aromatic species. Mass spectra of these fractions showed in both experiments that only aromatic substitution products were present; these were of the empirical formula $C_7F_nH_{8-n}$ (where n=1-4). The low intensity of the m/e 69 and 51 peaks indicated the absence of $CF_3$ or $CF_2H$ groups in these compounds with the observed intensities of these peaks being due to $C_4FH_2$ and $C_4H_3$ ions. From the reaction using a higher ratio of $NF_4BF_4$ to toluene, a significant amount of $C_6F_4H_2$ was found indicating some displacement of $CH_3$ from the ring. The NMR spectra of these products confirmed that various fluorotoluenes were present approximately in the amounts given (%): o-$C_6FH_4CH_3$(15), p-$C_6FH_4CH_3$(16), m-$C_6FH_4CH_3$ (8), 2,4-difluorotoluene (30), other di- and tri-fluorotoluenes (25), and 2,4,5,6-tetrafluorotoluene(7).

EXAMPLE III $C_6H_6$. Benzene and $NF_4BF_4$ were reacted using the same two techniques described for toluene. It was not possible to prevent charring and blackening of the benzene. Nevertheless, isolation of the volatile products condensable at −78° C. and examination of their mass spectra showed that substantial substitution of H by F had occurred, resulting in the formation of $C_6F_nH_{6-n}$(n=1-5). $C_6F_6$ was not observed and only minor amounts of the addition products $C_6F_6H_2$ and $C_6F_7H$ were observed.

In consideration of the aforementioned detailed description, it is obvious that the present invention provides a novel method for substituting fluorine atoms for hydrogen atoms in an aromatic ring structure without affecting saturated or oxidized substituents. The results of this invention clearly demonstrates the utilization of $NF_4^+$ion containing salts as powerful reagents for the introduction of fluorine atoms into aromatic rings by electrophilic substitution. Up to five hydrogens can be substituted in aromatic systems by a rapid substitution reaction, found to be highly efficient and relatively safe, before a much slower addition reaction takes over.

This slower fluorine addition reaction was also studied and found to produce the corresponding cyclo-hexadienes and hexenes. The addition reactions are novel and offer a controlled, high yield path to dienes which have previously only been obtained as parts of complex mixtures.

To obtain more data on the reactions of aromatics with $NF_4^+$ salts, an examination of aromatic systems, which were already highly fluorinated, was carried out. It was found that these starting materials are more inert toward the strongly fluorinating $NF_4BF_4$, thus allowing better control of the reaction. Experiments were carried out using tetra-, penta-, and hexafluorobenzene as starting materials. All reacted gradually at, or near, ambient temperature. All solutions and products were colorless throughout the reactions. Liberated NF$_3$ and excess, unreacted NF$_4$BF$_4$ were recoverable. The products were identified spectroscopically and most of them have been reported in the literature, making their identification unequivocal. The overall results are shown by the equations.

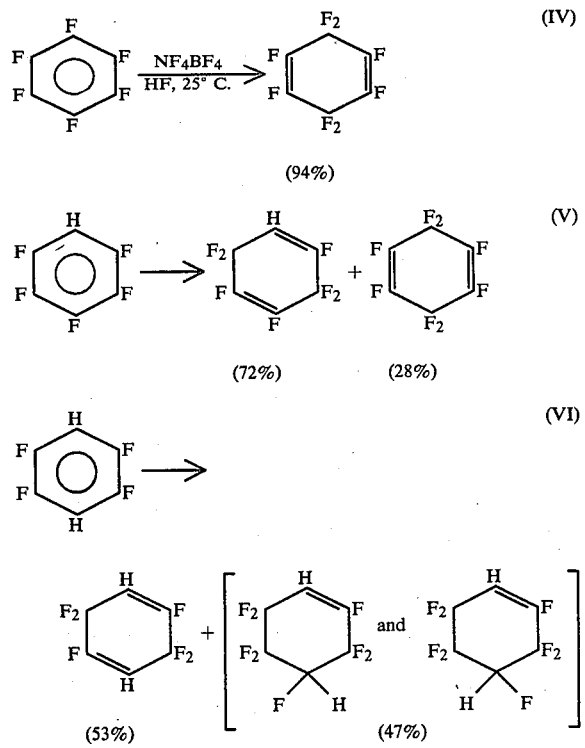

For these three highly fluorinated benzenes, the addition of the first two fluorines occurs in para position to each other (1,4 addition) and ortho to any hydrogen, if present. The addition of a second pair of fluorines cannot proceed by a 1, 4 mechanism without changing the ring into a bicyclo form, which is generally encountered only under photolytic conditions. Thus, the second pair of fluorines undergoes a 1, 2 addition to yield a cyclohexene.

For pentafluorobenzene, some substitution was also observed. It is not clear whether this is the result of a true substitution or of a addition-elimination reaction. In the case of p-C$_6$F$_4$H$_2$, the second F$_2$ addition produces the 1H,4H-octafluorocyclohexene which has two possible geometric isomers. Trace quantities of the saturated product, C$_6$F$_{10}$H$_2$, were also detected by mass spectroscopy.

In order to provide greater detail in connection with the addition reactions referred to above, Examples IV, V and VI are presented. In these addition reactions, almost no hydrogen substitutions occurred. The addition of the first pair of fluorine atoms always gave 1,4-cyclohexadiene in which the CF$_2$ group was ortho to hydrogen on the ring. The addition of the second pair of fluorine atoms results in the formation of cyclohexenes. These reactions occurred in high yield. All products were characterized spectroscopically and by comparison to literature data.

EXAMPLE IV

C$_6$F$_6$. A sample of NF$_4$BF$_4$ (4.07 mmol) contained in a Teflon (FEP) ampoule was dissolved in anhydrous HF (4 ml) and cooled to $-78°$ C., Hexafluorobenzene (1.25 mmol) was condensed into the ampoule which was then warmed gradually while stirring magnetically. After being kept overnight at 0°–10° C., the clear, colorless solution was cooled to $-78°$ C. and the volatile material quickly removed by condensation into a $-196°$ C. trap. The $-196°$ C. trap contained NF$_3$ (1.24 mmol) contaminated with traces of HF as shown by infrared spectroscopy. The reaction was allowed to continue for another day at room temperature. While maintaining the reaction ampoule at 0° C., the volatile products and HF were separated by fractional condensation in a series of U-traps cooled at $-45$, $-78$, and $-196$ . The $-196°$ C. fraction, NF$_3$ and HF, was discarded and the $-45°$ C. trap was empty. The $-78°$ C. trap contained a white solid, which melted to a colorless liquid above 0° C. Examination of this material by infrared and gas chromatography showed it to be 1,4 perfluorocyclohexadiene (1.18 mmol, 94.3% yield, based on C$_6$F$_6$) with a slight amount (2–3%) of unreacted C$_6$F$_6$. Intense ions in the mass spectrum were observed at m/e (assign.):224(C$_6$F$_8$), 205(C$_6$F$_7$), 186(C$_6$F$_6$) 155(C$_5$F$_5$, base), 136(C$_5$F$_4$), 124(C$_4$F$_4$), 117(C$_5$F$_3$), 105(C$_4$F$_3$), 93(C$_3$F$_3$), 86(C$_4$F$_3$), 74(C$_3$F$_2$), 69(CF$_3$), 55(C$_3$F), and 31(CF). The $^{19}$F NMR spectrum showed two equal area multiplets at 113.1 and 158.3 ppm in agreement with the literature for 1,4-C$_6$F$_8$. A white solid remained in the reaction ampoule and was shown by Raman spectroscopy to be NF$_4$BF$_4$ (1.48 mmol).

EXAMPLE V

C$_6$F$_5$H. As before, a mixture of NF$_4$BF$_4$ (4.29 mmol) and C$_6$F$_5$H (1.35 mmol) in HF was stirred and warmed during several hours from $-78°$ C. toward ambient temperature where it was kept for 12 hours. Evolved NF$_3$ (3.3 mmol) was monitored. After several more hours of stirring at room temperature, the products were separated by vacuum fractionation through U-traps cooled at $-45$, $-78$, and $-196°$ C. All material passed the $-45°$ trap except for a small amount of NF$_4$BF$_4$ remaining in the reactor. The $-196°$ C. fraction was discarded. The $-78°$ C. trap contained 1.24 mmol of a colorless liquid whose infrared spectrum indicated that it was composed of more than one cyclohexene [1170(ms), 1740(s), and 1720 cm$^{-1}$(vs)], as well as unreacted C$_6$F$_5$H. Gas chromatography showed three components which were analyzed individually by mass spectroscopy. In order of elution they were; (1) 1,4-C$_6$F$_8$, 26.1%, (2) 1H-heptafluorocyclohexa-1,4-diene, 66.3%, and (3) C$_6$FH, 7.6% with the composition based on GC peak areas. The mass spectra of the fractions agreed very well with published data for the assigned compounds. In addition, the $^{19}$F NMR spectra confirmed the formulated structures. For 1-H heptafluoro-cyclohexa-1,4-diene, a literature report of the NMR spectrum could not be found, but by comparison with related compounds it was apparent that the observed resonances and area ratios were reasonable for that structure. Chemical shifts of H or F, ppm or δ (rel. F peak area): 1-H, 5.93; 2-F, 127.7(1); 3-F, 115.2(2); 4-F, 160(1); 5-F, 155(1), 6-F, 101.7(2). The conversion of the C$_6$F$_5$H was 92%. The composition of the product was 28% 1,4-C$_6$F$_8$ and 72% 1, 4-C$_6$F$_7$H, with a total of 91% of the organic material being recovered.

EXAMPLE VI p-$C_6F_4H_2$. A mixture of $NF_4BF$(4.18 mmol) and p-$C_6F_4H_2$(1.43 mmol) in 4 ml HF at $-78°$ C. was stirred and warmed to $0°°$ C. over 3 hours, followed by overnight stirring at $0°-20°$ C. Fractional condensation at $-78°$ C. and $-196°$ C. was used to separate HF and $NF_3$ from the products which were retained in the $-78°$ C. trap. No unreacted $NF_4BF_4$ remained in the reactor. The original $-78$-$20$ C fraction was further separated by refractionating through $-45$ and $-78°$ C. traps. The former contained 0.21 mmol of a colorless liquid whose infrared spectrum showed a strong band at 1710 cm$^{-1}$ typical for the double bond of a —CF=CH—group. Analysis using GC/MS procedures showed this material to be 1H, 4H-hexafluorocyclohexa-1,4-diene. Prominent mass spectral peaks were found at m/e (assign.): 188($C_6F_6H_2$), 169($C_6F_5H_2$), 150($C_6F_4H_2$), 138($C_5F_4H_2$), 137($C_5F_4H$), 119($C_5F_3H_2$, base), 99($C_5F_2H$), 94($C_3F_3H$), 93($C_3F_3$), 88($C_4F_2H_2$), 81($C_5FH_2$), 80($C_5FH$), 75($C_3F_2H$), 69($CF_3$), 68($C_4FH$), 61($C_5H$), 57($C_3FH_2$), 56($C_3FH$), 51($CF_2H$), 50($CF_2$), 44($C_2FH$), and 31($CF$). The $^{19}F$ NMR spectrum for this compound agreed with published data. Similar analysis of the $-78°$ C. fraction showed it to be a mixture of unreacted p-$C_6F_4H_2$, the above described 1H,4H cyclohexa-1,4-diene, and a compound of empirical formula $C_6F_8H_2$. An infrared spectrum of the latter compound showed bands at cm$^{-1}$(intens.): 3070(w), 2960(w), 1710(ms), 1380(s), 1355(w), 1260(m), 1150(s), 1065(m), 1030(m), 743(mw), 637(w), 580(w), and 582(w). The bands near 3000 cm$^{-1}$ are assignable to the carbon-hydrogen stretches of —C=C—H and C—H groups while the 1710 cm$^{-1}$ peak is typical of a —CF=CH—stretching vibration. Strong ion peaks in the mass spectrum were at m/e (assign.): 226($C_6F_8H_2$), 207($C_6F_7H_2$), 186($C_6F_6$), 157($C_5F_5H_2$) 144($C_4F_5H$), 137($C_5F_4H$), 119($C_5F_3H_2$), 117($C_5F_3$), 113($_4F_4H$), 94($C_3F_3H$), 93($C_3F_3$), 75($C_3F_2H$), 69($CF_3$), 57($C_3FH_2$), 51($CF_2H$), and 50($CF_2$). The NMR spectra of the $-78°$ fraction confirmed the presence of p—$C_6F_4H_2$, 1H,4H-hexafluorocyclohexa-1,4-diene, and 1H,4H-octafluorocyclohexene; chemical shift of H or F,ppm or (rel. area) of 1H,4-$C_{6F8}H_2$:1-H,5.1(1); 2-F, 121.5(1), 3-F, 118.1(2), 4-H, 4.7(1), 4-F, 134.4(1), 5-F, 130.3(2), 6-F, 110.4(2). The conversion of starting material was 78%. The composition of the products was 53% $C_6F_6H_2$ and 47% $C_6F_8H_2$, with a total of 92% of the organic material being recovered.

As will be clearly evident to those skilled in the art, various alterations and modifications of the present invention can be made without departing from the spirit thereof, since it is intended that the invention be limited only by the scope of the appended claims.

What is claimed is:

1. A process for adding flourine across the double bonds in a highly halogenated aromatic hydrocarbon which comprises the step of effecting an addition reaction between a highly halogenated aromatic hydrocarbon and a hydrogen fluoride solvent solution of $NF_4BF_4$.

2. A process in accordance with claim 1 wherein said highly halogenated aromatic hydrocarbon is tetrafluorobenzene.

3. A process in accordance with claim 1 wherein said highly halogenated aramatic hydrocarbon is pentafluorobenzene.

4. A process in accordance with claim 1 wherein said highly halogenated aromatic hydrocarbon is hexafluorobenzene.

* * * * *